United States Patent [19]
Kiener

[11] Patent Number: 5,264,362
[45] Date of Patent: Nov. 23, 1993

[54] MICROBIOLOGICAL PROCESS FOR THE PRODUCTION OF 6-HYDROXYNICOTINIC ACID

[75] Inventor: Andreas Kiener, Visp, Switzerland

[73] Assignee: Lonza Ltd., Gampel/Valais, Switzerland

[21] Appl. No.: 960,812

[22] Filed: Oct. 14, 1992

Related U.S. Application Data

[62] Division of Ser. No. 848,215, Mar. 10, 1992.

[30] Foreign Application Priority Data

Mar. 18, 1991 [CH] Switzerland ............... 811/91

[51] Int. Cl.$^5$ ............... C12N 1/12; C12P 1/01; C12P 17/12
[52] U.S. Cl. ............... 435/252.1; 435/122; 435/123; 435/822
[58] Field of Search ............... 435/122, 123, 252.1, 435/822

[56] References Cited

U.S. PATENT DOCUMENTS

| | | | |
|---|---|---|---|
| 4,259,451 | 3/1981 | Steenbergen et al. | 435/822 |
| 4,567,140 | 1/1986 | Voelskow et al. | 435/252.4 |
| 5,104,798 | 4/1992 | Kiener | 435/124 |
| 5,135,858 | 8/1992 | Yamada et al. | 435/128 |
| 5,166,060 | 11/1992 | Roehl et al. | 435/122 |
| 5,173,412 | 12/1992 | Kiener et al. | 435/822 |

FOREIGN PATENT DOCUMENTS

| | | | |
|---|---|---|---|
| 0152948 | 8/1985 | European Pat. Off. | 435/122 |
| 0152949 | 8/1985 | European Pat. Off. | 435/122 |
| 0187680 | 7/1986 | European Pat. Off. | . |
| 0434035 | 6/1991 | European Pat. Off. | 435/122 |
| 0498316 | 8/1992 | European Pat. Off. | 435/122 |
| 3280891 | 12/1991 | Japan | 435/122 |
| 3280892 | 12/1991 | Japan | 435/122 |
| 664754 | 3/1988 | Switzerland | . |

OTHER PUBLICATIONS

Setliff et al., J. of Chem. and Eng. Data, vol. 21, No. 2, (1976), pp. 246 and 247.
Drews, G., Mikrobiologisches Praktikum [Microbiological Workshop], 4th Ed., Springer Verlag (1983).
Nagasawa et al., vol. 54, No. 7, (1988), pp. 1766 to 1769.

*Primary Examiner*—Herbert J. Lilling

[57] ABSTRACT

A microbiological process for the production of 6-hydroxynicotinic acid starting from 3-cyanopyridine. For this process, new microorganisms are used, which are capable of growing with 3-cyanopyridine as the sole carbon, nitrogen and energy source and of biotransforming it as substrate in 6-hydroxynicotinic acid.

5 Claims, No Drawings

MICROBIOLOGICAL PROCESS FOR THE PRODUCTION OF 6-HYDROXYNICOTINIC ACID

This is a divisional application of Ser. No. 07/848,215, filed on Mar. 10, 1992.

Background Of The Invention

1. Field Of The Invention

The invention relates to a new microbiological process for the production of 6-hydroxynicotinic acid, starting from 3-cyanopyridine, as well as to new microorganisms suitable for the process.

2. Background Art

6-Hydroxynicotinic acid is an important intermediate product for the production of 5,6-dichloronicotinic acid [Swiss Patent No. 664,754], which in turn is a starting product for pharmaceutically-active ingredients [Setcliff et al., J. of Chem. and Eng. Data, Vol. 21, No. 2, (1976), page 246]. So far, neither chemical nor microbiological processes for the production of 6-hydroxynicotinic acid starting from 3-cyanopyridine are known.

BROAD DESCRIPTION OF THE INVENTION

The main object of the invention is to provide a simple microbiological process for the production of 6-hydroxynicotinic acid starting from 3-cyanopyridine. Other objects and advantages of the invention are set out herein or are obvious herefrom to one ordinarily skilled in the art.

The objects and advantages of the invention are achieved by the process and microorganisms of the invention.

The invention involves microorganisms (biologically pure cultures thereof) that are capable of growing with 3-cyanopyridine as the sole carbon, nitrogen and energy source and of converting 3-cyanopyridine as the substrate to 6-hydroxynicotinic acid. Preferably the microorganism is the one deposited with the designation Agrobacterium sp. in the DSM with the deposit number 6336, and descendants and mutants thereof.

The invention also involves a microbiological process for the production of 6-hydroxynicotinic acid. 3-Cyanopyridine is biotransformed with the microorganisms of the invention to 6-hydroxynicotinic acid. The latter is accumulated in the medium. Preferably the effective enzymes of the microorganisms are induced with 3-cyanopyridine. Preferably the reaction takes place under substrate addition once or continuously so that the substrate concentration does not exceed 20 percent by weight. Preferably the reaction is performed at a pH of 4 to 10 and a temperature of 10° to 50° C.

DETAILED DESCRIPTION OF THE INVENTION

According to the invention, all microorganisms are suitable that are capable of growing with 3-cyanopyridine as the sole carbon, nitrogen and energy source and of converting 3-cyanopyridine as the substrate to 6-hydroxynicotinic acid. These microorganisms are an embodiment of the invention and can be selected and isolated with the help of usual microbiological techniques, for example, from sewage treatment plants, with 3-cyanopyridine as the growth substrate. The phrase "microorganisms which are capable of growing with 3-cyanopyridine as the sole carbon, nitrogen and energy source" comprises both mixtures of microorganisms and pure-isolates of microorganisms, that are used under sterile or non-sterile fermentation conditions.

Suitably, the microorganism Achromobacter sp., which, based on more detailed identification data, is designated below as Agrobacterium sp., (DSM 6336), and descendants and mutants thereof are used. The microorganism Agrobacterium sp. DSM 6336 was deposited with the Deutsche Sammlung für Mikroorganismen und Zellkulturen GmbH [German Collection for Microorganisms and Cell Cultures GmbH] (DSM), Mascheroderweg 1b, D-3300 Brunswick on Jan. 31, 1991 with the designation DSM 6336.

A scientific (taxonomic) description of Agrobacterium sp. DSM 6336 is:

| Properties of the strain: | |
|---|---|
| cell shape | rods |
| width, micron | 0.6 to 0.8 |
| length, micron | 1.5 to 3.0 |
| mobility | + |
| gram reaction | − |
| lysis by 3 percent KOH | + |
| aminopeptidase (Cerni) | + |
| spores | − |
| oxidase | + |
| catalase | + |
| growth | |
| anaerobic | − |
| 37°/41° C. | +/− |
| pH 5.6 | − |
| MacConkey broth | + |
| SS agar | − |
| Cetrimide agar | − |
| 2 percent NaCl | + |
| pigments | − |
| nondiffusing | − |
| diffusing | − |
| fluorescent | − |
| pyocyanine | − |
| acid from (OF test) | |
| aerobic glucose | − |
| anaerobic glucose | − |
| gas from glucose | − |
| acid from (ASA) | |
| glucose | + |
| fructose | + |
| xylose | + |
| m-erythritol | + |
| melezitose | − |
| arabinose | + |
| saccharose | − |
| cellobiose | + |
| trehalose | − |
| rhamnose | + |
| dulcitol | − |
| sorbitol | + |
| glycerol | + |
| L-arabinose | + |
| fructose | + |
| glucose | + |
| mannose | + |
| maltose | + |
| xylose | + |
| saccharose | + |
| sorbose | − |
| mannitol | + |
| 2-ketogluconate | − |
| N-acetylglucosamine | + |
| L-serine | − |
| hydroxybutyrate | − |
| L-lysine | + |
| L-ornithine | + |
| ADH | − |
| ADC | − |
| ONPG | − |
| VP | − |
| indole | − |
| NO$_2$ from NO$_3$ | + |
| denitrification | + |

| -continued | |
|---|---|
| Properties of the strain: | |
| phenylalanine desaminase | k.W. |
| lecithinase | − |
| urease | + |
| Simmons citrate | − |
| malonate | − |
| ketolactose | − |
| hydrolysis of | |
| starch | − |
| gelatin | − |
| casein | − |
| DNA | − |
| Tween 80 | − |
| aesculin | + |
| alkalization of litmus milk | − |
| growth substance requirement | − |
| use of substrate | |
| acetate | + |
| adipate | − |
| caprate | − |
| citrate | − |
| glycolate | − |
| lactate | + |
| laevulinate | − |
| malate | + |
| malonate | − |
| phenylacetate | − |
| suberate | − |

The process for the production of 6-hydroxynicotinic acid is performed according to the invention in such a way that 3-cyanopyridine with one of the above microorganisms is biotransformed to 6-hydroxynicotinic acid and the latter is accumulated in the medium.

Before the actual reaction the microorganisms are usually cultivated (cultured) and the effective enzymes of the microorganisms are suitably induced with 3-cyanopyridine. Usually the cultivation (culture) and induction take place with 3-cyanopyridine in a concentration of 0.01 to 20 percent by weight, preferably of 0.1 to 1 percent by weight.

Then the microorganisms can be harvested either before the substrate addition (3-cyanopyridine) by usual separation processes or the substrate (3-cyanopyridine) can be directly added to the microorganisms.

For the actual process, the cell suspension is then suitably adjusted to an optical density at 650 nm of 1 to 100, preferably of 5 to 80. As the medium, those usual among experts, preferably one of the media whose composition is given in Tables 1 and 2 (below), are used. The substrate (3-cyanopyridine) for the production of 6-hydroxynicotinic acid can be added once or continuously. Suitably, the substrate addition takes place so that the substrate concentration in the medium does not exceed 20 percent by weight, preferably so that it does not exceed 10 percent by weight. Usually the reaction of 3-cyanopyridine to 6-hydroxynicotinic acid takes place with dormant cells. The pH of the reaction suitably is in a range of 4 to 10, preferably in a range of 5 to 9. Suitably the reaction is performed at a temperature of 10° to 50° C., preferably at a temperature of 20° to 40° C.

After a usual reaction time of 1 to 100 hours, 6-hydroxynicotinic acid can be isolated, for example, by acidification of the cell-free fermentation solution.

EXAMPLE 1

Isolation Of 3-Cyanopyridine-Metabolizing Microorganisms

Aerobic 3-cyanopyridine-metabolizing microorganisms were concentrated in the A+N medium (see Table 1 below) with the addition of 0.1 percent (w/v) 3-cyanopyridine as sole carbon and energy source. The general techniques for isolating microorganisms are described, for example, in G. Drews, Mikrobiologisches Praktikum [Microbiological Workshop], 4th edition, Springer Verlag, (1983). Samples from sewage treatment plants were used as an inoculum. The concentrations were cultivated in shaking flasks at 30° C. After inoculating three times in fresh medium, the concentrations were plated out on the same medium with the addition of 16 g of agar per liter and incubated at 30° C. After repeated plating out on agar medium, pure cultures were able to be isolated.

TABLE 1

| A + N medium | |
|---|---|
| Composition | Concentration (mg/l) |
| $(NH_4)_2SO_4$ | 2000 |
| $Na_2HPO_4$ | 2000 |
| $KH_2PO_2$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| pyridoxal hydrochloride | $10 \cdot 10^{-3}$ |
| riboflavin | $5 \cdot 10^{-3}$ |
| nicotinic acid amide | $5 \cdot 10^{-3}$ |
| thiamine hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.6H_2O$ | $20 \cdot 10^{-3}$ |
| $Na_2MoO_4.2H_2O$ | $30 \cdot 10^{-3}$ |
| $EDTANa_2.2H_2O$ | $5 \cdot 10^{-3}$ |
| $FeSO_4.7H_2O$ | $2 \cdot 10^{-3}$ |
| (The pH of the solution was adjusted to 7.0.) | |

EXAMPLE 2

Reaction Of 3-Cyanopyridine To 6-Hydroxynicotinic Acid (a) Agrobacterium Sp. (DSM No. 6336) was cultured in A+N medium (see Table 1 below) with the addition of 0.1 percent (w/v) 3-cyanopyridine in a fermenter at pH 7 and at a temperature of 30° C. Then the cells were centrifuged off, resuspended in A+N medium and adjusted on an optical density of 10 at 650 nm. This cell suspension was poured into a shaking flask and mixed with 0.1 mol/l (10.4 g/l) of 3-cyanopyridine. After an incubation of 16 hours at 30° C. on a shaking machine, 0.06 mol/l (8.3 g/l) of 6-hydroxynicotinic acid was detected by analytical methods in the cell-free solution, which corresponded to a yield of 66 percent, relative to the 3-cyanopyridine used.

(b) Agrobacterium sp. (DSM No. 6336) was cultivated in a mineral salt medium (see Table 2 below) with the addition of 0.1 percent (w/v) 3-cyanopyridine in a fermenter (working volume 5.5 liters) at pH 7 and a temperature of 30° C. A solution consisting of 1 mol/l of sulfuric acid and 2 mol/l of 3-cyanopyridine and a solution of 3 mol/l of sodium hydroxide was added for the pH adjustment. After 20 hours of growth (cultivation), the optical density at 650 nm was 5.0 and neither 3-cyanopyridine nor 6-hydroxynicotinic acid were detectable. At this time 3-cyanopyridine (100 g, 1 mol)

was put in the fermenter. After an additional incubation of 6 hours, 3-cyanopyridine (100 g, 1 mol) was again added. After an additional 12 hours, this microorganism suspension (biomass) was centrifuged off and the supernatant acidified to pH 2.0 to precipitate the 6-hydroxynicotinic acid. Altogether 269 g of 6-hydroxynicotinic acid was isolated, corresponding to a yield of 96 percent relative to the 3-cyanopyridine used.

TABLE 2

| Components | Concentration |
| --- | --- |
| Composition of the mineral salt medium | |
| $MgCl_2.6H_2O$ | 0.8 g/l |
| $CaCl_2$ | 0.16 g/l |
| $Na_2SO_4$ | 0.25 g/l |
| $KH_2PO_4$ | 0.4 g/l |
| $Na_2HPO_4$ | 0.9 g/l |
| SLF | 1 ml/l |
| FeEDTA | 15 ml/l |
| Composition of the trace elements (SLF) the mineral salt medium | |
| KOH | 15 g/l |
| $EDTANa_2.2H_2O$ | 100 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2$ | 0.18 g/l |
| $Na_2MoO_4.2H_2O$ | 0.2 g/l |
| Composition of FeEDTA | |
| $EDTANa_2.H_2O$ | 5 g/l |
| $FeSO_4.7H_2O$ | 2 g/l |
| (The pH of the solution was adjusted to 7.0.) | |

What is claimed is:

1. Agrobacterium sp. deposited in the DSM with the deposit number 6336, or a descendant thereof or a mutant thereof, the Agrobacterium sp. DSM 6336 or the descendant thereof or the mutant thereof being capable of growing with 3-cyanopyridine as a sole carbon, nitrogen and energy source and of converting 3-cyanopyridine as a substrate to 6-hydroxynicotinic acid, and said Agrobacterium sp. DSM 6336 or descendant thereof or the mutant thereof which is in purified and isolated form.

2. A biologically pure culture of Agrobacterium sp. deposited in the DSM with the deposit number 6336, or a descendant thereof or a mutant thereof, the Agrobacterium sp. DSM 6336 or the descendant thereof or the mutant thereof being capable of growing with 3-cyanopyridine as a sole carbon, nitrogen and energy source and of converting 3-cyanopyridine as a substrate to 6-hydroxynicotinic acid.

3. The Agrobacterium sp. DSM 6336 or the descendant thereof or the mutant thereof as claimed in claim 1 wherein effective enzymes of the microorganism have been induced with 3-cyanopyridine.

4. The Agrobacterium sp. DSM 6336 as claimed in claim 1.

5. The biologically pure culture of Agrobacterium sp. DSM 6336 as claimed in claim 1.

* * * * *